United States Patent
Smith et al.

Patent Number: 5,109,868
Date of Patent: May 5, 1992

[54] METHOD FOR DIAGNOSING SENILE DEMENTIA OF THE ALZHEIMER'S TYPE

[75] Inventors: Anthony D. Smith, Iffley; Kim A. Jobst, Oxford, both of England

[73] Assignee: E. R. Squibb & Sons, Inc., Princeton, N.J.

[21] Appl. No.: 670,627

[22] Filed: Mar. 18, 1991

[51] Int. Cl.$^5$ .............................................. A61B 5/103
[52] U.S. Cl. ................................ 128/774; 128/661.05
[58] Field of Search .................... 128/660.07, 661.03, 128/661.05, 731, 732, 774

[56] References Cited

PUBLICATIONS

DeCarli et al, "Critical analysis of the us of computer-assisted transverse axial tomography to study human brain in aging and dementia of the Alzheimer type," Neurology 1990; 40:872-882.

Prohovnik et al, "Cerebral perfusion as a diagnostic marker of early Alzheimer's disease," Neurology 1988; 28:931-937.

Perani et al, "Technetium-99m-HMPAO-SPECT study of regional cerebral perfusion in early Alzheimer's disease," J. Nucl. Med., Sep. 1988; 29:1507-1514.

Kido et al, "temporal lobe atrophy in patients with Alzheimer disease: a CT study," Amer. J. Neuroradiol., 1989; 10:551-555.

de Leon et al, "Early marker for Alzheimer's disease: the atrophic hippocampus," Lancet 1989; ii:672-673.

George et al, "CT diagnostic features of Alzheimer's disease: importance of the choroidal/hippocampal fissure comples," Amer. J. Neuroradiol, 1990; 11:101-107.

Hoffman et al, "<F-18>-Fluorodeoxyglucose (FDG) and positron emission tomography (PET) in aging and dementia—A decade of studies," Eur. Neurol., 1989; 29:16-24.

McGeer et al, "Fluorodeoxyglucose-18 positron emission tomography studies in presumed Alzheimer cases, including 13 serial scans," Canad. J. Neurol. Sci., 1990; 17:1-11.

Burns et al, "The investigation of Alzheimer's disease with single photon emission tomography," J. Neurol. Neurosurg. Psychiat., 1989; 52:248-253.

Hunter et al, "The pattern of function-related regional cerebral blood flow investigated by single photom emission tomography with Tc-99M-HMPAO in patients with presenile Alzheimer's disease and Korsakoff's psychosis," Phychol. Med., 1989; 19:847-855.

Esiri et al, "A quantitative study of the neurofibrillary tangles and the choline acetyltransferase activity in the cerebral cortex and the amygdala in Alzheimer's disease," J. Neurol. Neurosurg. Psychiat., 1990; 53:161-165.

*Primary Examiner*—Max Hindenburg
*Attorney, Agent, or Firm*—Burton Rodney

[57] ABSTRACT

A method is provided for detecting senile dementia of the Alzheimer's type (SDAT) wherein atrophy of the medial temporal lobe of the brain (for example as determined by CT scan) as indicated by a thickness thereof, at its narrowest point, of 11.5 mm or less represents a positive finding of SDAT. In an extension of such method, atrophy of the medial temporal lobe as described above combined with reduced blood flow in the posterior parietal/superior temporal cortex (for example as determined by SPET), represents a positive finding of SDAT.

13 Claims, 3 Drawing Sheets

METHOD FOR DIAGNOSING SENILE DEMENTIA OF THE ALZHEIMER'S TYPE

FIELD OF THE INVENTION

The present invention relates to a method for diagnosing senile dementia of the Alzheimer's type (SDAT) wherein atrophy of the medial temporal lobe of the brain alone or together with reduced blood flow in the posterior parietal/superior temporal cortex represents a positive finding of SDAT.

BACKGROUND OF THE INVENTION

Computed tomography (CT) has revealed that many demented patients with a clinical diagnosis of Alzheimer's disease display more marked cerebral atrophy than expected for their age (DeCarli et al "Critical analysis of the use of computer-assisted transverse axial tomography to study human brain in aging and dementia of the Alzheimer type," Neurology 1990; 40:872-883). Functional changes in demented patients have been found by methods such as positron emission tomography (PET) and single photon emission tomography (SPET) that show cerebral blood flow, glucose or oxygen uptake, or uptake of radioligands: the most frequent finding is a functional deficit in the posterior parietal and temporal lobes of the cortex (Hoffman et al "<F-18>-Fluorodeoxyglucose (FDG) and positron emission tomography (PET) in aging and dementia—A decade of studies," Eur. Neurol., 1989;29:16-24; McGeer et al, "Fluorodeoxyglucose-18 positron emission tomography studies in presumed Alzheimer cases, including 13 serial scans," Canad. J. Neurol. Sci., 1990; 17:1-11; Prohovnik et al, "Cerebral perfusion as a diagnostic marker of early Alzheimer's disease," Neurology 1988;28:931-937; Perani et al, "Technetium-99m-HMPAO-SPECT study of regional cerebral perfusion in early Alzheimer's disease," J. Nucl. Med. 1988;29:1507-1514) Single photon emission tomography (SPET) has recently been used to show that the functional deficits in the posterior parietal and lateral temporal lobes (as indicated by reduced blood flow) are related to the degree of cognitive decline (Burns et al, "The investigation of Alzheimer's disease with single photon emission tomography," J. Neurol. Neurosurg. Psychiat., 1989;52:248-253; Hunter et al, "The pattern of function-related regional cerebral blood flow investigated by single photon emission tomography with Tc-99M-HMPAO in patients with presenile Alzheimer's disease and Korsakoff's psychosis," Psychol. Med., 1989;19:847-855; Montaldi et al, "Measurements of regional cerebral blood flow and cognitive performance in Alzheimer's disease," J. Neurol. Neurosurg. Psychiat., 1990;53:33-38). Such findings are difficult to reconcile with neuropathological studies which show that the most severely affected parts of the brain in Alzheimer's disease are in the medial temporal lobe, mainly the amygdala, the hippocampal formation and adjacent parahippocampal gyrus as indicated by a high concentration of plaques and tangles and reduced tissue mass (Brun et al, "Regional pattern of degeneration in Alzheimer's disease: neuronal loss and histopathological grading," Histopathology, 1981;5:549-564; Wilcock et al, "Plaques, tangles and dementia. A quantitative study," J. Neurol. Sci., 1982;56:343-356; Hyman et al, "Cell-specific pathology isolates the hippocampal formation," Science, 1984;225:1168-1170; Ball et al, "A new definition of Alzheimer's disease: a hippocampal dementia," Lancet, 1985;i:14-16; Esiri et al, "A quantitative study of the neurofibrillary tangles and the choline acetyltransferase activity in the cerebral cortex and the amygdala in Alzheimer's disease," J. Neurol. Neurosurg, Psychiat., 1990;53:161-165). Atrophy of these areas can be revealed in life by CT studies in which the scan angle is adjusted to give a clearer view of the medial temporal lobe. Such studies on patients with a clinical diagnosis of Alzheimer's disease have indeed shown severe damage to structures in the medial temporal lobe (LeMay, M., "CT changes in dementing diseases: a review," Amer. J., Neuroradiol. 1986;7:841-853; Kido et al, "Temporal lobe atrophy in patients with Alzheimer disease: a CT study," Amer. J. Neuroradiol., 1989;10:551-555; de Leon et al, "Early marker for Alzheimer's disease: the atrophic hippocampus," Lancet 1989;ii:672-673; George et al, "CT diagnostic features of Alzheimer's disease: importance of the choroidal/hippocampal fissure complex," Amer. J. Neuroradiol, 1990;11:101-107). However, atrophy of the medial temporal lobe is also found in other conditions, notably epilepsy and hypoxia (Esiri and Oppenheimer, "Diagnostic Neuropathology," Oxford, Blackwell Scientific Publications, 1989), schizophrenia (Roberts, G. W., "Schizophrenia—The cellular biology of a functional psychosis," Trends Neurosci., 1990;13:207-211), amnesia (Press et al, "Hippocampal abnormalities in amnesic patients revealed by high-resolution magnetic resonance imaging," Nature, 1989;341:54-57) and, perhaps, depression (Bowen et al, "Circumscribed changes of the cerebral cortex in neuropsychiatric disorders of later life," Proc. Nat. Acad. Sci. USA, 1989;86: 9504-9508) and so is not unique to dementia of Alzheimer's type.

The CT and SPET studies described above have each been carried out on different groups of patients and not on the same patients.

DESCRIPTION OF THE INVENTION

In accordance with the present invention, a method is provided for detecting senile dementia of the Alzheimer's type (SDAT) wherein atrophy of the medial temporal lobe of the brain as indicated by a reduced thickness or narrowing thereof as measured at its most narrow point represents a possible positive finding of SDAT.

Further, in accordance with the present invention, a method is provided for detecting SDAT wherein atrophy of the medial temporal lobe as described above combined with reduced blood flow (or a perfusion deficit) in the parietotemporal cortex represents a possible positive finding of SDAT.

The term "senile dementia of the Alzheimer's type" (also referred to as "Alzheimer-type" dementia and includes Alzheimer's disease) as employed herein and as defined in the Merck Manual, Fifteenth Edition, 1987, refers to a degenerative process marked by cognitive impairment together with a large loss of cells from the cerebral cortex and other brain areas including marked atrophy and wide sulci, dilated ventricles, senile plaques and neurofibrillary tangles.

In carrying out the method of the present invention, the medial temporal lobe of the brain of the patient is studied, such as by computed tomography (CT) or magnetic resonance imaging (MRI) to obtain a visual representation or scan thereof. The scan is then analyzed to determine the thickness or width of the left and/or right medial temporal lobe (hippocampal formation and parahippocampal gyrus) at the narrowest point adjacent to the brain stem. The measurement may be compared to a similar measurement in normal non-demented age-matched controls. If the thickness or width of the right and/or left medial temporal lobes of the patient is at least about 25% below the average thickness of the corresponding medial temporal lobe of normal non-demented age-matched controls (that is a ratio of the medial temporal lobe of patient to control is less than about 0.75:1), this would indicate atrophy of the medial temporal lobe and thus a positive finding of SDAT. If it is found from the CT scan that the measured thickness of the left and/or right medial temporal lobe is 11.5 mm or less, this would indicate atrophy of the medial temporal lobe and thus a positive finding of SDAT.

In addition, in carrying out the method of the invention, to confirm the diagnosis of SDAT, the parietotemporal cortex of the patient will be examined, for example, by single photon emission tomography (SPET) to determine blood flow or perfusion of the cortex. A reduced blood flow or perfusion deficit in the parietotemporal cortex (which is considered mild to severe as determined and described in the accompanying Example) combined with atrophy of the medial temporal lobe as discussed above will be a positive finding of SDAT.

EXAMPLE

Figure 1:
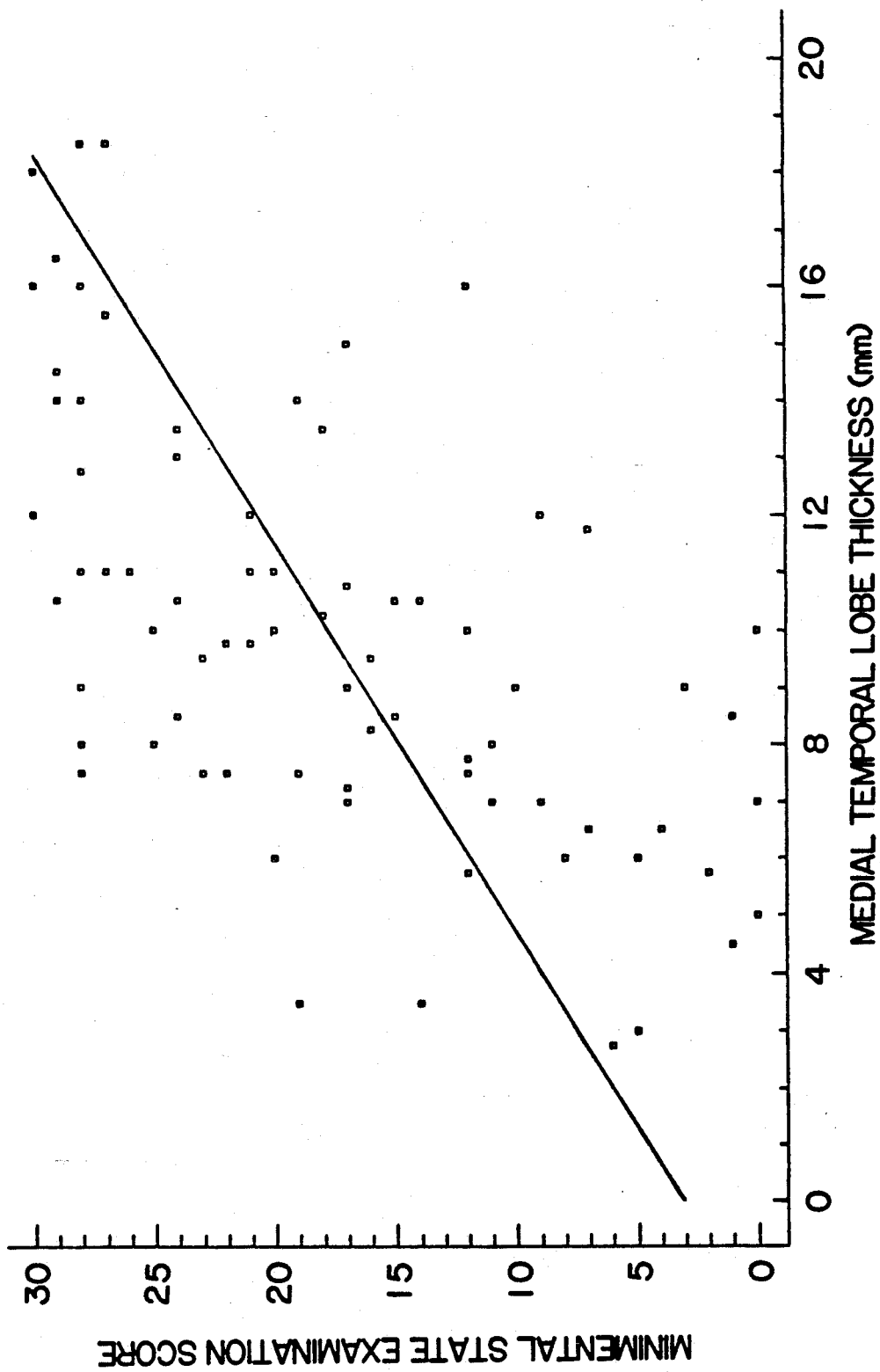
FIGS. 1 to 3 are graphs showing relationship of cognitive test scores to medial temporal lobe thickness measured by CT.

The following example describes CT studies on the temporal lobe and SPET studies on parietal/superior temporal perfusion of the cortex in the same group of patients. These studies were carried out to establish if there was any relationship between atrophy of the medial temporal lobe and a perfusion deficit in the parietotemporal cortex and, if so, whether such a relationship was associated with Alzheimer's disease defined clinically and, where possible, by histopathological criteria.

Patients and Methods

Subjects with varying degrees of mental deterioration and memory loss underwent detailed screening with a view to making a diagnosis. Diagnoses were made according to DSM-III-R criteria. Medication remained unchanged during screening.

Each person underwent a detailed clinical and psychiatric history, full physical examination of all systems, routine blood tests to exclude identifiable metabolic causes of memory loss and dementia and neuropsychological screening using the Cambridge Mental Disorders of the Elderly Examination (CAMDEX) [Roth, et al: "CAMDEX: The Cambridge examination for mental disorders of the elderly," 72 pp. Cambridge, Cambridge University Press, 1988]. Screening specifically included computed tomography (CT and single photon emission tomography (SPET) scanning of the brain.

Computed tomography (CT) scans were carried out in the axial plane with 4 mm contiguous sections through the posterior fossa and 8 mm contiguous sections through the cerebrum parallel to the orbito-meatal line. Following this procedure and starting with a lateral topogram, sections were taken passing through the front of the hard palate and top of the mastoids in 4 mm parallel sections through the temporal lobes. This scan plane is approximately 20 degrees caudad to the orbito-meatal line. Left and right medial temporal lobe width (hippocapal formation and parahippocampal gyrus) were then measured in mm using calipers at the narrowest point adjacent to the brainstem. Measurements were made blind to the clinical diagnosis. All scans were reported by a neuro-radiologist for evidence of any intra-cerebral pathology.

SPET studies were carried out using an intravenous injection of Technetium 99m (500 MBq) hexamethyl-propyleneamine oxime (HMPAO) given as a bolus and prepared according to the manufacturer's instructions (Ceretec, exametazime, Amersham International). Subjects were injected in a sitting position in a quiet normally lit room. If a subject was unable to lie still for twenty minutes (14 patients) between five and twenty milligrams of intravenous diazepam was given at least five minutes after the injection of 99m-TcHMPAO. In 4 cases some diazepam had been given a few hours earlier to facilitate CT scanning. After injection with HMPAO the subject was placed supine with the orbito-meatal line as vertical as possible and with the head held still using a pillow containing fine polystyrene balls from which the air had been extracted. SPET was then performed using an IGE-400T rotating gamma camera and Nuclear Diagnostics software. Sixty-four images were obtained over 360 degrees, each with a 20 second acquisition time and $64 \times 64$ pixels in resolution. Transverse and coronal slices were reconstructed by filtered back projection and were 2 pixels in width (13 mm). SPET scans were assessed blind to the clinical diagnosis using a scale of zero to three, where 0 represented no perfusion deficit, 1 a minimal deficit, 2 a mild to moderate deficit and 3 a severe perfusion deficit breaching the cortex. In order to localize and grade the deficits more accurately scans were assessed in both transverse and coronal planes. Grading was done alongside the CT scan so as to exclude those perfusion deficits where there was clearly discernible intracerebral pathology (such as a cerebral infarct) to account for the observed SPET perfusion anomaly. SPET perfusion deficits in the left, right or bilateral parieto-temporal region with a grading of 2 or more were considered significant for the purpose of subsequent analysis.

Each subject was assessed using the CAMDEX administered by one of the research nurses or doctors, in the subject's home or at the initial screening visit in the hospital. The CAMDEX enables the derivation of a number of scores. The cognitive section CAMCOG, includes sections for testing memory, praxis, language, attention and concentration and has a maximum score of 107. It also enables the derivation of the Mini Mental State Examination (MMSE) which is scored out of 30. Significant cognitive deficit was thought to be indicated by a score of less than 80 in the CAMCOG and less than 24 in the MMSE.

Results

Clinical Diagnosis

Fifty-one of the 79 patients fulfilled the DSM-III-R criteria for senile dementia of the Alzheimer type SDAT, and could be further subdivided, as shown in Table 1, into those who were thought to have SDAT alone and those with other CNS disease as well. Ten patients had dementia not thought to be primarily SDAT, including 5 who initially presented with dementia but who had significant psychiatric symptoms consistent with a diagnosis of pseudodementia (Table 1). Eighteen patients were not thought to have a cognitive deficit consistent with a diagnosis of dementia, of whom two had CT evidence of a cerebrovascular accident and one had had neurosurgery in the parietal region.

Cognitive testing gave average scores ($\pm$SD) for the demented group (n=61) of 51$\pm$28 (range 0-96) for CAMCOG and 15$\pm$8 (range 0-29) for MMSE; for the non-demented group (n-18) the corresponding scores were 98$\pm$6 (range=77-105) and 28.5$\pm$1.5 (range 25-30).

Computed Tomography

The mean of the average thickness of left and right medial temporal lobes in the 51 patients with SDAT was 8.5$\pm$2.8 (SD) mm range 2.75-15). The median value was significantly different ($P<0.0001$ Mann-Whitney) from that of the 18 non-demented patients, whose mean medial temporal lobe thickness was 14.7$\pm$3.0 mm (range 10-18.5). On this basis, a medial temporal lobe thickness of 11.5 mm or less was provisionally defined as indicative of significant atrophy. Using this criterion, 49 out of the 51 patients with SDAT had medial temporal lobe atrophy on one or both sides, as did 6 out of 10 of the other demented patients. However, only 5 out of 18 non-demented patients had medial temporal lobe atrophy; one of these five non-demented patients had evidence of cerebral infarction extending to the temporal lobe that could have accounted for the atrophy (Table 1).

The above clearly establishes that significant atrophy of the medial temporal lobe is a positive indication of SDAT.

Single Photon Emission Tomography

Using the scale devised for scoring the SPET scans for the degree of perfusion deficit in the parietotemporal region, 44 out of the 51 patients with SDAT and 4 out of 10 of the other demented patients had a significant deficit on one or both sides (Table 1). None of the demented group showed CT evidence of focal ischaemia or surgery that would have accounted for the changes seen on SPET. Five out of the 18 non-demented patients had a significant parietotemporal perfusion deficit, but the deficit could be accounted for in 3 of these by other pathology. Thus, 2 of the 3 had CT evidence of infarction in the parietal region and 1 had had surgery in the parietal lobe.

Although the location of the perfusion deficit in the posterior cortex varied slightly between patients, it generally included parts of the superior parietal lobe, the angular and supramarginal gyri and the middle temporal gyrus.

Figure 2:
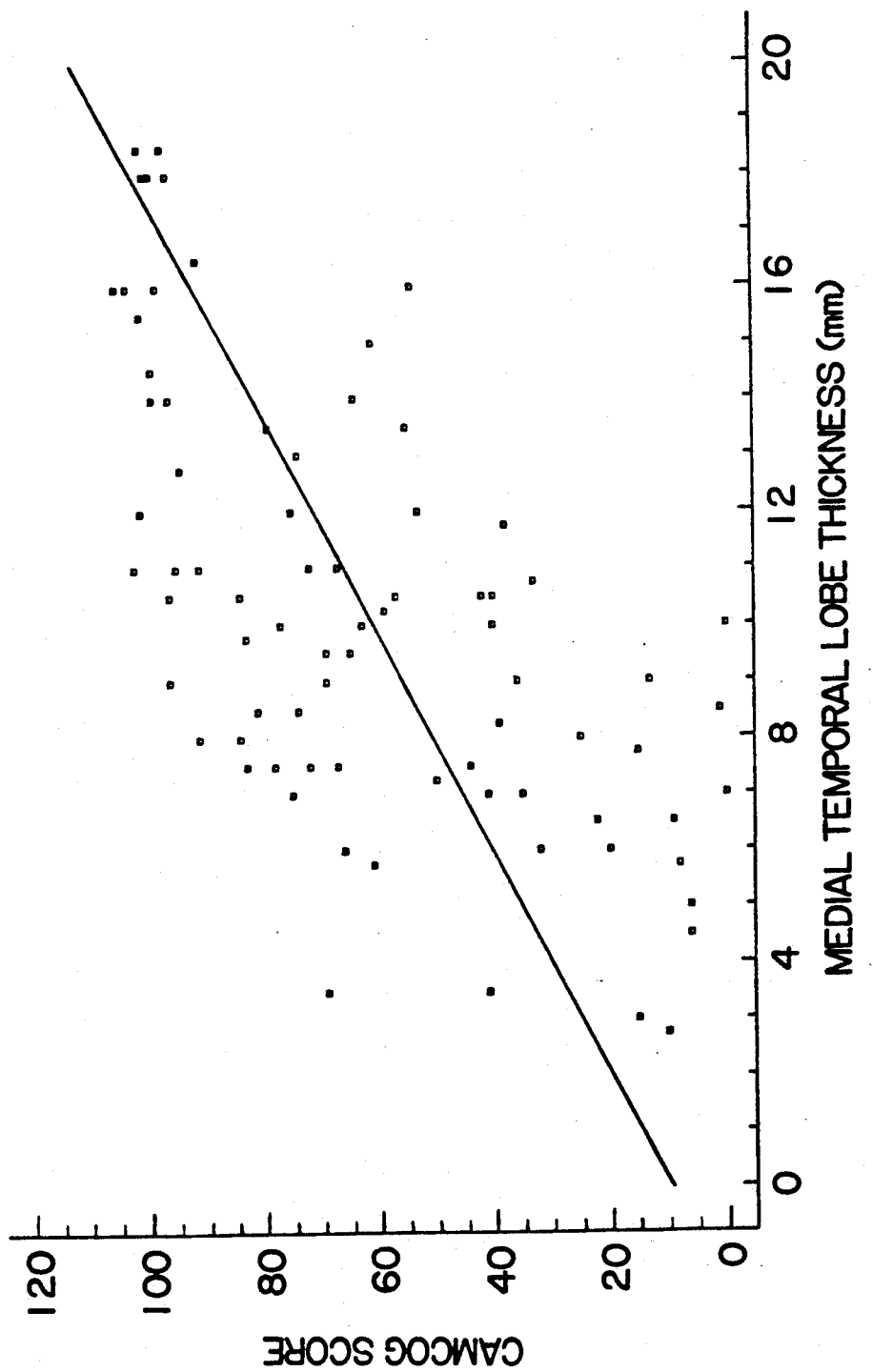
Figure 3:
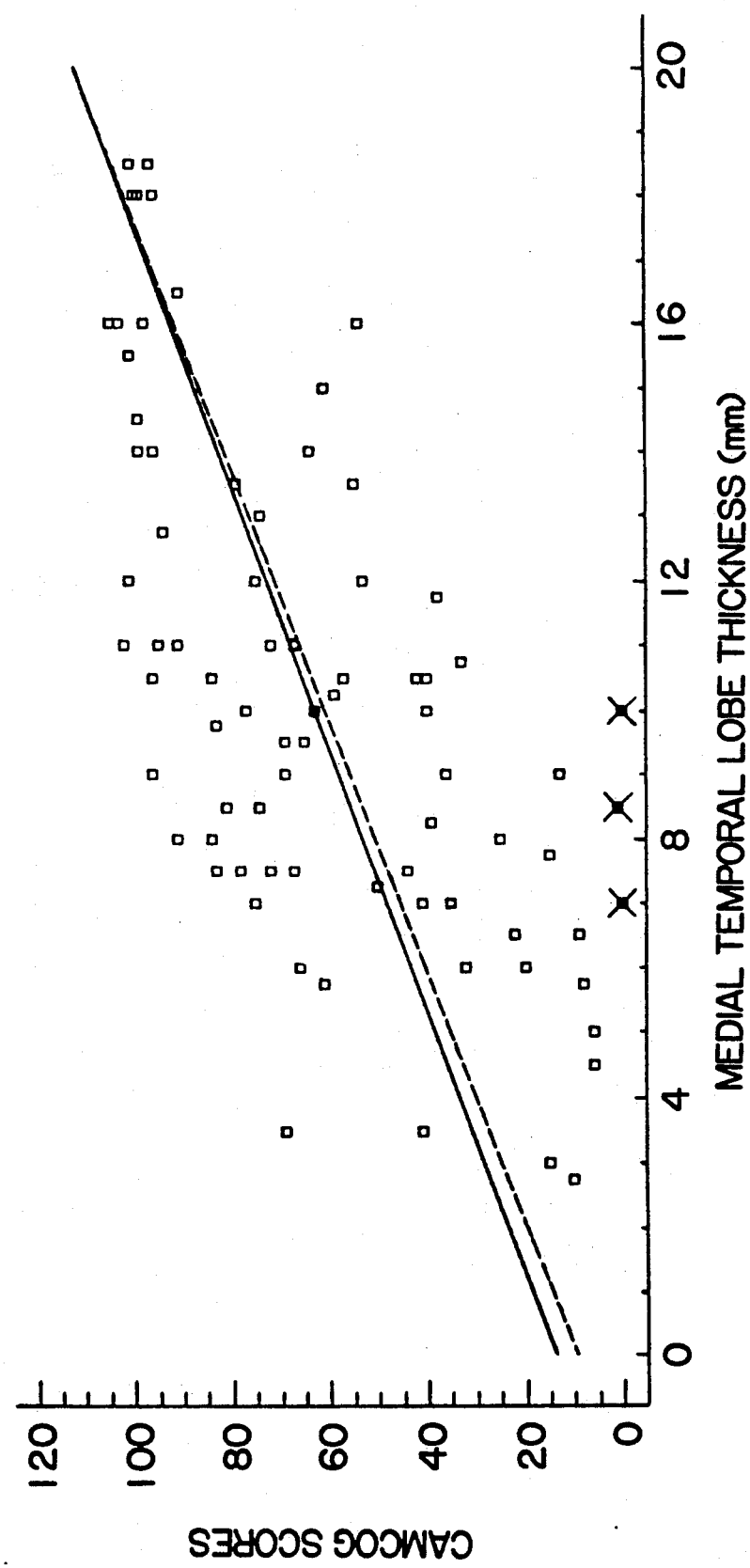

Analysis of Cognitive Test Data Relative to Thickness of Medial Temporal Lobe The medial temporal lobe thickness measured on CT scans as the thinnest point of the medial temporal lobe as seen by the eye, in mm, was plotted against the score on MMSE (FIG. 1), and against the score on CAMCOG (FIGS. 2 and 3) for the first 79 patients in the study.

Statistical analysis of the data showed that there was a linear relationship between the medial temporal lobe thickness and each of the cognitive test scores; in all cases the slope of the line was highly ($P<00000.1$) significantly different from zero. The correlation coefficients were as follows:

Medial temporal lobe thickness versus MMSE:0.625 with R squared=40.2%

Medial temporal lobe thickness versus CAMCOG:0.64 with R squared=39.1%.

R-squared is an indication that the thickness of the medial temporal lobe contributes approximately by that % to the cognitive score.

Comparison of CT and SPET Changes in the Same Patient

All 44 of the patients who had significant parietotemporal perfusion deficits on SPET also displayed significant atrophy of one or both medial temporal lobes as shown by CT. Thus, only five of the 49 SDAT patients who had atrophy of the medial temporal lobe did not show a significant perfusion deficit in the parietotemporal region (Table 1); however, all 5 of these patients had a SPET perfusion score of 1 either on one or on both sides, which on the aforementioned classification represented a slight perfusion deficit. All 23 patients who were considered to have SDAT without other CNS disease displayed a combination of medial temporal lobe atrophy (lobe thickness of 11.5 mm or less on one or both sides) and significant parietotemporal perfusion deficit. Two patients classified as having SDAT together with other CNS disease showed neither atrophy of the medial temporal lobe nor a significant perfusion deficit in the parietotemporal lobe, but both had unusual clinical features in addition to SDAT.

In subjects where there was medial temporal lobe atrophy (i.e. thickness of 11.5 mm or less on one or both sides), a comparison was made between the left and right sides to see if there was any relationship between asymmetrical medial temporal lobe atrophy and perfusion changes revealed by SPET. Asymmetry of the atrophy was arbitrarily considered significant if the difference between the sides was 3 mm or more. Using this criterion, 13 of the 60 subjects with medial temporal lobe atrophy showed asymmetry (7 with more on the left). In 12 out of these 13 patients, SPET scans showed that the parietotemporal blood flow ipsilateral to the atrophy was lower than on the other side. The remaining subject showed a symmetrical perfusion deficit in the parietotemporal region.

Histopathology

Ten of the 51 patients with a clinical diagnosis of SDAT have died: nine fulfilled the histopathological criteria of Z. S. Khachaturian, ("Diagnosis of Alzheimer's disease," Arch. Neurol., 1985;42:1097-1105) for Alzheimer's disease and the other probably had normal pressure hydrocephalus. All ten of these patients showed the combination of medial temporal lobe atrophy and parietotemporal perfusion deficit. Two patients out of the 10 demented patients without SDAT have died. One of these patients had a clinical diagnosis of multi-infarct dementia but had a histopathological diagnosis of Alzheimer's disease; this patient also showed medial temporal lobe atrophy and a parietotemporal perfusion deficit in life, as well as CT evidence of cerebral ischemia. The other patient had a clinical diagnosis of progressive supranuclear palsy, confirmed at post-mortem, and did not show the combination of medial temporal lobe atrophy and parietotemporal perfusion deficit.

TABLE 1

Results for patients in different diagnostic categories.

| | Total | CT MTL atrophy | SPET change | Both CT and SPET |
|---|---|---|---|---|
| CLINICALLY DEMENTED | | | | |
| SDAT alone | 23 | 23 | 23 | 23 |
| SDAT/isch. | 19 | 18 | 15 | 15 |
| SDAT/other | 9 | 8 | 6 | 6 |
| Multi-infarct | 3 | 3 | 3 | 3 |
| PSP | 2 | 1 | 0 | 0 |
| Pseudodementia | 5 | 2 | 1 | 1 |
| NOT CLINICALLY DEMENTED | | | | |
| Lesion absent | 15 | 4 | 2 | 2 |
| CVA etc. | 3 | 1# | 3* | 1# |

*Two of these patients had a CVA and one had previous surgery that could account for the abnormal SPET scans.
This patient had a CVA that could account for the atrophy of the MTL.

Patients were divided into categories according to the clinical diagnosis. Patients were considered to have atrophy of the medial temporal lobe on CT if the thickness of one or both lobes was 11.5 mm or less. A significant change in the SPET scan of the parietotemporal region on either side was defined by the scoring procedure described in Methods. Abbreviations: CVA cerebrovascular accident; isch. ischaemia; MTL, medial temporal lobe; SDAT, senile dementia of Alzheimer's type; SDAT/other, SDAT plus other CNS disease; PSP, progressive supranuclear palsy.

Discussion

The CT findings of atrophy of the medial temporal lobe are in agreement with several recent studies on demented patients who are presumed to have Alzheimer's disease (Kido 89, supra, de Leon, 89 supra, George, 90 supra), although a relatively simple measurement that can be made directly from the film was used herein. Likewise, the SPET studies agree with a large body of literature in which a variety of tracers have been used to show reduced perfusion or uptake of tracer, particularly in the posterior parietotemporal region, of patients with a clinical diagnosis of Alzheimer's disease (Gemmel et al, "Single photon emission tomography with $^{123}$I-isopropylamphetamine in Alzheimer's disease and multi-infarct dementia," Lancet 1984;ii:1348; Neary et al, "Single photon emission tomography using $^{99m}$Tc-HMPAO in the investigation of dementia," J. Neurol. Neurosurg. Psychiat., 1987;50:1101-1109; Perani 88, supra, Leys et al, "Single photon emission tomography with HMPAO Tc$^{99m}$ in Alzheimer's disease," Rev. Neurol., 1989;145:443-45; Burns 89, supra, Hellman et al, "Alzheimer disease—quantitative analysis of I-123-iodoamphetamine SPECT brain imaging," Radiology, 1989;172:183-188; Hunter 89, supra, Montaldi 19, supra).

The striking feature of the results was the frequent occurrence of these two changes in the same patient. Both the CT and SPET changes often occurred in the same patient if the patient was clinically demented and particularly if the patient had dementia of Alzheimer's type. 86% (44/51) of patients with dementia of Alzheimer's type had a combination of medial temporal lobe atrophy and reduced parietotemporal blood flow, while only four out of the 10 demented patients who did not have a clinical diagnosis of Alzheimer's disease showed this combination, one of whom was found to have Alzheimer's disease upon autopsy (see below). Such a combination of changes was rare in patients who were not demented, occurring in only two out of 18 patients if one excluded the patient where the changes might be accounted for by focal ischaemic damage in the medial temporal lobe.

A combination of medial temporal lobe atrophy and reduced parietotemporal blood flow in the same patient may thus be indicative of Alzheimer's disease, if due account is taken of clinical and CT evidence of ischaemic damage as a possible causative factor. Consistent with this suggestion is the finding that, out of the 12 patients who have died, the ten with a histological diagnosis of Alzheimer's disease all displayed the combination of CT evidence of atrophy of the medial temporal lobe with SPET evidence of a parietotemporal perfusion deficit. It is noteworthy that the patient who has died in the group classified clinically as having multi-infarct dementia in fact has a histological diagnosis of Alzheimer's disease and also displayed the combination of CT and SPET changes.

A causal relationship between the two changes may be indicated by the finding that in 12 out of 13 patients where the atrophy of the medial temporal lobe was more severe on one side than on the other, there was a similar asymmetry in the parietotemporal perfusion deficit. It is suggested that the reduced parietotemporal blood flow might reflect pathological change in the projection neurons in the parahippocampal gyrus which, in monkeys (Mesulam, et al, "Limbic and sensory connections of the inferior parietal lobule (area PG) in the rhesus monkey: a study with a new method for horseradish peroxidase histochemistry," Brain Res., 1977;136:393-414; Cavada et al, "Posterior parietal cortex in Rhesus monkey.1. Parcellation of areas based on distinctive limbic and sensory corticocortical connections," J. comp. Neurol., 1989;287:393-421), have been shown to innervate inferior parietal areas equivalent (Eidelberg et al, "Interior parietal lobule. Divergent architectonic asymmetries in the human brain," Archiv. Neurol., 1984;41:843-852) to the supramarginal and angular gyri in man. It has been pointed out that the neurons that are pathologically affected in Alzheimer's disease are predominantly projection neurons that interconnect association and limbic areas of the cortex (Pearson et al, "Anatomical correlates of the distribution of the pathological changes in the neocortex in Alzheimer's disease," Proc. Nat. Acad. Sci. USA, 1985;82:4531-4534; Esiri 1990, supra) and that the pyramidal neurons of the hippocampal formation and parahippocampal gyrus are particularly severely affected (Hyman et al, "Perforant pathway changes and the memory impairment of Alzheimer's disease," Ann. Neurol., 1986;20:472-481; Esiri 1990, supra). Medial temporal lobe atrophy in dementia might follow the loss of the latter projection neurons, whereas in other conditions where such atrophy occurs (as described hereinbefore), it might be due to the loss of different neurons. The above finding suggests that, at least in the parietal lobe, one consequence of the damage or loss of projection neurons in the parahippocampal gyrus might be reduced metabolism and blood flow in the target area. As the disease progresses, the loss of input from the hippocampal region might in turn lead to trasneuronal pathological changes in the parietal lobe, which appear to be more severs in the later stages of Alzheimer's disease (Brun 1981, supra; Najlerahim et al, "Biochemical measurements in Alzheimer's disease reveal a necessity for improved neuroimaging techniques to study metabolism," Biochem. J., 1988;251:305-308; Bowen 1989, supra). An alternative explanation for the combination of changes described herein is that the changes in the medial temporal lobe are a consequence of retrograde degeneration originating from an abnormality in the parietal lobe but in that case one might have expected to find that reduced blood flow in the parietotemporal region was more common than atrophy of the hippocampal region, whereas in this study the opposite was found.

What is claimed is:

1. A method for detecting senile dementia of the Alzheimer's type (SDAT), which comprises measuring the thickness of one or both medial temporal lobes of the brain of a patient, and determining if the thickness of one or both medial temporal lobes is at least about 25% below the average thickness of the medial temporal lobe of a significant number of normal non-demented controls, thereby signifying presence of SDAT in such patient, or determining if the thickness of both medial temporal lobes of the patient is not more than about 25% below the average thickness of the medial temporal lobe of a significant number of normal non-demented controls, thereby signifying absence of SDAT in said patient.

2. The method as defined in claim 1 including the step exposing the brain of a patient to a CT scan to obtain a visual representation of the medial temporal lobe of the patient, measuring the thickness of the medial temporal lobe at the thinnest point thereof as shown on the CT scan, and comparing the thickness of the medial temporal lobe of the patient with the average thickness of the medial temporal lobe of age-matched controls.

3. The method as defined in claim 1 wherein the left and/or right medial temporal lobe width (hippocampal formation and parahippocampal gyrus) is measured in said patient at the narrowest point adjacent to the brain stem and this measurement is compared to a similar measurement of age-matched controls.

4. The method as defined in claim 1 wherein the medial temporal lobe thickness of the patient is about 11.5 mm or less on one or both sides indicating SDAT.

5. A method for diagnosing for senile dementia of the Alzheimer's type (SDAT), including the steps of determining the thickness of the medial temporal lobe of the brain of a patient, said thickness being measured along a predetermined section of such lobe, comparing said thickness of the medial temporal lobe of said patient with the average thickness of the medial temporal lobe of age-matched controls measured along said predetermined section of said lobe, determining if the ratio of said thickness of the medial temporal lobe of the patient to the average thickness of the medial temporal lobe of said age-matched controls is less than about 0.75:1, and if so making a positive diagnosis for SDAT, and if said ratio is greater than about 0.75:1, making a negative diagnosis for SDAT.

6. The method as defined in claim 5 including the step of exposing the patient to a CT scan to obtain a visual representation of said medial temporal lobe.

7. The method as defined in claim 5 wherein the width of the left and/or right medial temporal lobe width (hippocampal formation and parahippocampal gyrus) is measured in said patient at the narrowest point adjacent to the brain stem and this measurement is compared to a similar measurement of age-matched controls.

8. The method as defined in claim 5 wherein the medial temporal thickness of the patient is about 11.5 mm or less on one or both sides indicating SDAT.

9. A method for diagnosing for senile dementia of the Alzheimer's type (SDAT), including the steps of conducting a CT scan of the brain of a patient to obtain a visual representation of the medial temporal lobe, and measuring the left and/or right medial temporal lobe width (hippopcamal formation and parahippocampal gyrus) at the narrowest point adjacent to the brain stem, whereby a thickness measurement of one or both sides of the medial temperal lobe of 11.5 mm or less indicates a positive finding for SDAT, and a thickness measurement of both sides of the medial temporal lobe of greater than about 11.5 mm or more indicates a negative finding for SDAT.

10. A method for detecting senile dementia of the Alzheimer's type (SDAT), which comprises determining the thickness of the medial temporal lobe of a patient as a measure of possible atrophy of the medial temporal lobe, and in the same patient determining degree of blood flow in the posterior parietal/superior temporal cortex as a measure of possible perfusion deficit in the parietotemporal region, and wherein there are detected both atrophy of the medial temporal lobe and perfusion deficit in the parietotemporal region, making a positive diagnosis of SDAT.

11. The method as defined in claim 10 including the step of exposing the brain of said patient to a CT scan to obtain a visual representation of the medial temporal lobe thickness and to a SPET scan to obtain a visual representation of the blood flow in the parietotemporal region.

12. The method as defined in claim 11 wherein results of the CT scan show that the ratio of the thickness of one or both of the medial temporal lobes of the patient to the average thickness of the medial temporal lobe of age-matched controls is below about 0.75:1, thereby indicating atrophy of the medial temporal lobe, and the blood flow to the parietotemporal region is at a mild to severe perfusion deficit, thereby indicating a positive finding of SDAT.

13. The method as defined in claim 11 wherein the thickness of one or both of the medial temporal lobe at its narrowest point is 11.5 mm or less and the blood flow to the parietotemporal region on one or both sides is at a mild to severe perfusion deficit, thereby indicating a positive finding of SDAT.

* * * * *

UNITED STATES PATENT AND TRADEMARK OFFICE
CERTIFICATE OF CORRECTION

PATENT NO. : 5,109,868

DATED : May 5, 1992

INVENTOR(S) : Anthony D. Smith et al.

It is certified that error appears in the above-identified patent and that said Letters Patent is hereby corrected as shown below:

Column 10, line 5-6, after "lobe", delete "width".

Signed and Sealed this

Twenty-eighth Day of September, 1993

Attest:

BRUCE LEHMAN

Attesting Officer

Commissioner of Patents and Trademarks